United States Patent [19]
LaValle

[11] Patent Number: 5,384,118
[45] Date of Patent: Jan. 24, 1995

[54] GEL HAIRDRESSING COMPOSITION

[76] Inventor: Lila S. LaValle, 7705 Hiawatha La., Rockville, Md. 20855-2601

[21] Appl. No.: 119,659

[22] Filed: Sep. 13, 1993

[51] Int. Cl.$^6$ .............................................. A61K 7/06
[52] U.S. Cl. .............................. 424/70.13; 424/70.15; 424/401; 424/70.11; 514/944
[58] Field of Search ......................... 424/70, 71, 401; 514/944

[56] References Cited

U.S. PATENT DOCUMENTS

| | | | |
|---|---|---|---|
| 3,101,301 | 8/1963 | Siegal et al. | 424/70 |
| 3,427,382 | 2/1969 | Haefele | 424/71 |
| 4,810,503 | 3/1989 | Carson et al. | 424/76.3 |
| 4,855,130 | 8/1989 | Konrad et al. | 424/70 |
| 4,886,660 | 12/1989 | Patel et al. | 424/70 |
| 4,904,466 | 2/1990 | Carson et al. | 424/76.3 |
| 5,098,699 | 3/1992 | Hayama et al. | 424/71 |
| 5,102,660 | 4/1992 | Forestier et al. | 424/401 |

Primary Examiner—Thurman K. Page
Assistant Examiner—Robert H. Harrison

[57] ABSTRACT

A hairdressing gel composition includes a blend of measured quantities of the following ingredients: water, alcohol, PVP/VA copolymer, glycerin, surfactants, tetrasodium EDTA, carbomer 940, triethanolamine, coconut oil, lanolin, and vitamin E. The surfactants are selected from the group consisting of methyl gluceth-20, myreth-3 laurate, ceteth-20. More specifically, the composition may include a blend of deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, D&C yellow No. 10, petrolatum, vegetable oil, pure coconut oil, olive oil, mineral oil, microcrystalline wax, lanolin, and vitamin E.

3 Claims, No Drawings

GEL HAIRDRESSING COMPOSITION

BACKGROUND OF THE INVENTION

1. Field of the Invention

The present invention relates generally to hairdressing compositions, and, more particularly, to hairdressing compositions based on gel compositions.

2. Description of the Prior Art

Throughout the years, many different hairdressing compositions have been developed which employ a wide variety of ingredients. Yet, there are certain desirable features in a gel hairdressing compositions that do not appear to be available in the marketplace and do not appear to be disclosed in publications disclosing hairdressing compositions.

More specifically, hairdressing gels available in the marketplace give the user substantial control over their hair. However, when the gel dries, the hair often becomes stiff. Also, a flaky build up can accumulate on the hair and scalp, eventually dulling the hair's natural sheen. In this respect, it would be desirable if a hair gel composition were provided which precludes hair from becoming stiff. It would also be desirable if a hair gel composition were provided which precludes a flaky build up from accumulating. It would also be desirable if a hair gel composition were provided which precludes a dulling of the hair's natural sheen.

Another desirable feature of a hairdressing gel composition is that it would provide curl control. Such a gel composition could be used by people who have a permanent to control frizz that may occur, unmanageable hair, or simply as an everyday grooming product, especially after shampoo.

When a person shampoos one's hair, the hair is generally cleansed of most compositions that have been added since the last shampoo. In addition, the shampooing process also removes natural substances from the hair. As a result, freshly shampooed hair may be exceptionally hard to manage and control. In this respect, it would be desirable if a hair gel composition were provided which is useful for providing good control to freshly shampooed hair.

A specific gel hairdressing composition that has been marketed is known as Ban De Terre, manufactured by Zotos International, Inc., Darien, Conn. The ingredients of this composition include deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, and D&C yellow No. 10.

Another specific hairdressing composition that has been marketed is known as Coconut Oil by Hairlox. This composition includes petrolalum, vegetable oil, pure coconut oil, olive oil, mineral oil, microcrystalline wax, lanolin, and vitamin E.

With respect to publications disclosing hair gel compositions, the following U.S. Pat. Nos. are representative of some disclosures of hairdressing compositions: 3,427,382; 4,886,660; 4,855,130; and 5,098,699. More specifically, U.S. Pat. No. 3,427,382 discloses a gel hairdressing composition that includes a high molecular weight carboxyvinyl polymer, a hydroxy-propoxyl-substituted methylcellulose ether, and alcohol, and water. U.S. Pat. No. 4,886,660 discloses a stable shine hair conditioner that includes a $C_{14}$–$C_{22}$ alkyl trimethyl quaternary ammonium compound, mineral oil or glyceryl monostearate, a $C_{14}$–$C_{22}$ alkanol, a cellulose polymer, a copolymer of polyvinylpyrrolidone and vinyl acetate (PVP/VA), and a plasticizer selected from the group consisting of lanolin acetate, propylene glycol, glycerine, and water soluble lanolin in an aqueous vehicle. U.S. Pat. No. 4,855,130 discloses a hair treating composition that includes the amino acid glycine in combination with and aliphatic organic acid which is free of amino groups, e.g. citric acid, and a wax and/or oil component, e.g. petrolatum and fatty alcohols. U.S. Pat. No. 5,098,699 discloses a hair setting gel composition that includes a neutralized salt of a crosslinked carboxyvinyl polymer, an amphoteric resin, and a solvent comprised of water and a lower alcohol.

Although the above-listed U.S. Pat. Nos. (namely 3,427,382; 4,886,660; 4,855,130; and 5,098,699) differ markedly from the below disclosed compositions of the invention, the general teachings of these patents with respect to storing, measuring, and blending of hairdressing gel ingredients are generally applicable, and these patents are incorporated herein by reference.

Thus, while the foregoing body of prior art indicates it to be well known to use hairdressing gel compositions, the prior art described above does not teach or suggest a gel hairdressing composition which has the following combination of desirable features: (1) precludes hair from becoming stiff; (2) precludes a flaky build up from accumulating; (3) precludes a dulling of the hair's natural sheen; (4) provides curl control; and (5) provides good control to freshly shampooed hair. The foregoing desired characteristics are provided by the unique gel hairdressing composition of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved hairdressing gel composition which includes a blend of measured quantities of the following ingredients: water, alcohol, PVP/VA copolymer, glycerin, surfactants, tetrasodium EDTA, carbomer 940, triethanolamine, coconut oil, lanolin, and vitamin E. The surfactants may be selected from the group consisting of methyl gluceth-20, myreth-3 laurate, and ceteth-20.

In accordance with another aspect of the invention, a new and improved hairdressing gel composition includes a blend of deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, D&C yellow No. 10, petrolatum, vegetable oil, pure coconut oil, olive oil, mineral oil, microcrystalline wax, lanolin, and vitamin E.

This composition is obtained by blending 50% by weight of a blend of deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, and D&C yellow No. 10, with 50% by weight of a blend of petrolatum, vegetable oil, pure coconut oil, olive oil, mineral oil microcrystalline wax, lanolin, and vitamin E.

In accordance with another aspect of the invention, a new and improved hairdressing gel composition includes a blend of: 11.95–60.00% by weight of deionized water, 25.00–40.00% by weight of SD alcohol 40, 0.75–2.25% by weight of PVP/VA copolymer, 0.10–0.40% by weight of carrageenan, 5.00–15.00% by weight of glycerin, 0.10–0.40% by weight of panthenol, 0.10–0.40% by weight of dimethicone, 0.50–2.00% by weight of methyl gluceth-20, 0.50–2.00% by weight of myreth-3 laurate, 0.50–2.00% by weight of ceteth-20, 0.10–0.40% by weight of tetrasodium EDTA, 1.00–2.00% by weight of carbomer 940, 0.25–1.25% by weight of triethanolamine, 0.10–0.40% by weight of methylchloroisothiazolinone, 0.10–0.40% by weight of methylisothiazolinone, 0.25–1.25% by weight of styrene/acrylate copolymer, 1.00–3.00% by weight of petrolalum, 1.00–3.00% by weight of vegetable oil, 1.00–3.00% by weight of coconut oil, 1.00–3.00% by weight of olive oil, 1.00–3.00% by weight of mineral oil, 0.10–0.75% by weight of microcrystalline wax, 0.50–2.00% by weight of lanolin, and 0.05–0.15% by weight of vitamin E.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining some preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved gel hairdressing composition which has all of the advantages of the prior art and none of the disadvantages.

It is another object of the present invention to provide a new and improved gel hairdressing composition which may be easily and efficiently manufactured and marketed.

It is a further object of the present invention to provide a new and improved gel hairdressing composition which is of durable and reliable construction.

An even further object of the present invention is to provide a new and improved gel hairdressing composition which is susceptible of a low cost of manufacture with regard to both materials and labor, and which accordingly is then susceptible of low prices of sale to the consuming public, thereby making such gel hairdressing composition available to the buying public.

Still yet a further object of the present invention is to provide a new and improved gel hairdressing composition which precludes hair from becoming stiff.

Still another object of the present invention is to provide a new and improved gel hairdressing composition that precludes a flaky build up from accumulating.

Yet another object of the present invention is to provide a new and improved gel hairdressing composition which precludes a dulling of the hair's natural sheen.

Even another object of the present invention is to provide a new and improved gel hairdressing composition that provides curl control.

Still a further object of the present invention is to provide a new and improved gel hairdressing composition which provides good control to freshly shampooed hair.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying descriptive matter in which there are explained preferred embodiments of the invention.

DESCRIPTION OF THE PREFERRED EMBODIMENT

New and improved gel hairdressing compositions embodying the principles and concepts of the present invention will be described.

In accordance with the invention, there is provided a hairdressing gel composition, comprising a blend of: deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, D&C yellow No. 10, petrolalum, vegetable oil, pure coconut oil, olive oil, mineral oil, microcrystalline wax, lanolin, and vitamin E.

A suitable PVP/VA copolymer is described in the above-mentioned U.S. Pat. No. 4,886,660, incorporated herein by reference.

The deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, and D&C yellow No. 10 may be obtained from the gel hairdressing composition that has been marketed is known a Ban De Terre, manufactured by Zotos International, Inc., Darien, Conn.

The petrolatum, vegetable oil, pure coconut oil, olive oil, mineral oil, microcrystalline wax, lanolin, and vitamin E may be obtained from the non-gel hairdressing composition known as Coconut Oil by Hairlox.

Example 1

More specifically, a first exemplary composition made in accordance of the invention is made by blending 50% by weight of the Ban De Terre by Zotos and 50% by weight of the Coconut Oil by Hairlox. In this way, the Example 1 contains a blend of deionized water, SD alcohol 40, PVP/VA copolymer, clover blossom extract, bay laurel extract, carrageenan, glycerin, panthenol, dimethicone, methyl gluceth-20, myreth-3 laurate, ceteth-20, tetrasodium EDTA, carbomer 940, triethanolamine, methylchloroisothiazolinone, methylisothiazolinone, styrene/acrylate copolymer, fragrance, FD&C Blue No. 1, D&C yellow No. 10, petrolatum, vegetable oil, pure coconut oil, olive oil, mineral oil, microcrystalline wax, lanolin, and vitamin E.

Alternatively, a number individual ingredients can be obtained separately and blended together. The ingredients can be blended together in a range of proportions. For example, the following ingredients can be blended together in the respective ranges for each ingredient as indicated: 11.95–60.00% by weight of deionized water, 25.00–40.00% by weight of SD alcohol 40, 0.75–2.25% by weight of PVP/VA copolymer, 0.10–0.40% by weight of carrageenan, 5.00–15.00% by weight of glycerin, 0.10–0.40% by weight of panthenol, 0.10–0.40% by weight of dimethicone, 0.50–2.00% by weight of methyl gluceth-20, 0.50–2.00% by weight of myreth-3 laurate, 0.50–2.00% by weight of ceteth-20, 0.10–0.40% by weight of tetrasodium EDTA, 1.00–2.00% by weight of carbomer 940, 0.25–1.25% by weight of triethanolamine, 0.10–0.40% by weight of methylchloroisothiazolinone, 0.10–0.40% by weight of methylisothiazolinone, 0.25–1.25% by weight of styrene/acrylate copolymer, 1.00–3.00% by weight of petrolatum, 1.00–3.00% by weight of vegetable oil, 1.00–3.00% by weight of coconut oil, 1.00–3.00% by weight of olive oil, 1.00–3.00% by weight of mineral oil, 0.10–0.75% by weight of microcrystalline wax, 0.50–2.00% by weight of lanolin, and 0.05–0.15% by weight of vitamin E.

Example 2

More specifically, a second exemplary composition made in accordance of the invention is made by blending together the following ingredients in the amounts specified: 60.00% by weight of deionized water, 25.00% by weight of SD alcohol 40, 0.75% by weight of PVP/VA copolymer, 0.10% by weight of carrageenan, 5.00% by weight of glycerin, 0.10% by weight of panthenol, 0.10% by weight of dimethicone, 0.50% by weight of methyl gluceth-20, 0.50% by weight of myreth-3 laurate, 0.50% by weight of ceteth-20, 0.10% by weight of tetrasodium EDTA 1.00% by weight of carbomer 940, 0.25% by weight of triethanolamine, 0.10% by weight of methylchloroisothiazolinone, 0.10% by weight of methylisothiazolinone, 0.25% by weight of styrene/acrylate copolymer, 1.00% by weight of petrolatum, 1.00% by weight of vegetable oil, 1.00% by weight of coconut oil, 1.00% by weight of olive oil, 1.00% by weight of mineral oil, 0.10% by weight of microcrystalline wax, 0.50% by weight of lanolin, and 0.05% by weight of vitamin E.

Example 3

More specifically, a third exemplary composition made in accordance of the invention is made by blending together the following ingredients, disclosed in Example 2, in the amounts specified: 11.95 % by weight of dionized water, 40.00% by weight of SD alcohol 40, 2.25% by weight of PVP/VA copolymer, 0.40% by weight of carrageenan, 15.00% by weight of glycerin, 0.40% by weight of panthenol, 0.40% by weight of dimethicone, 2.00% by weight of methyl gluceth-20, 2.00% by weight of myreth-3 laurate, 2.00% by weight of ceteth-20, 0.40% by weight of tetrasodium EDTA, 2.00% by weight of carbomer 940, 1.25% by weight of triethanolamine, 0.40% by weight of methylchloroisothiazolinone, 0.40% by weight of methylisothiazolinone, 1.25% by weight of styrene/acrylate copolymer, 3.00% by weight of petrolatum, 3.00% by weight of vegetable oil, 3.00% by weight of coconut oil, 3.00% by weight of olive oil, 3.00% by weight of mineral oil, 0.75% by weight of microcrystalline wax, 2.00% by weight of lanolin, and 0.15% by weight of vitamin E.

Example 4

More specifically, a fourth exemplary composition made in accordance of the invention is made by blending together the following ingredients, disclosed in Examples 2 and 3, in the amounts specified: 36.00% by weight of deionized water, 32.15% by weight of SD alcohol 40, 1.50% by weight of PVP/VA copolymer, 0.25% by weight of carrageenan, 10.00% by weight of glycerin, 0.25% by weight of panthenol, 0.25% by weight of dimethicone, 1.00% by weight of methyl gluceth-20, 1.00% by weight of myreth-3 laurate, 1.00% by weight of ceteth-20, 0.25% by weight of tetrasodium EDTA, 1.50% by weight of carbomer 940, 0.75% by weight of triethanolamine, 0.25% by weight of methylchloroisothiazolinone, 0.25% by weight of methylisothiazolinone, 0.75% by weight of styrene/acrylate copolymer, 2.00% by weight of petrolatum, 2.00% by weight of vegetable oil, 2.00% by weight of coconut oil, 2.00% by weight of olive oil, 2.00% by weight of mineral oil, 0.5% by weight of microcrystalline wax, 1.00% by weight of lanolin, and 0.10% by weight of vitamin E.

By using the compositions of the invention, hair is left soft and manageable with no flaking or stiffness. To obtain the benefits of the compositions of the invention, it is not necessary to include all of the ingredients listed in Examples 2–4. More specifically, the following ingredients can be left out: carrageenan, panthenol, methylchloroisothiazolinone, methylisothiazolinone, styrene/acrylate copolymer, the coloring materials, petrolatum, vegetable oil, olive oil, mineral oil, and microcrystalline wax. By leaving out the just-mentioned ingredients, the composition of the invention can have the following ingredients: water, alcohol, PVP/VA copolymer, glycerin, dimethicone, methyl gluceth-20, myreth-3 laurate, ceteth-20, tetrasodium EDTA, carbomer 940, triethanolamine, coconut oil, lanolin, and vitamin E.

It is noted that methyl gluceth-20, myreth-3 laurate, and ceteth-20 are surfactants. In this respect other surfactants can be substituted for them as is well known in the art. It is also not necessary that the compositions of the invention contain dimethicone. Therefore, compositions of the invention include the following ingredients: water, alcohol, PVP/VA copolymer, glycerin, surfactants, tetrasodium EDTA, carbomer 940, triethanolamine, coconut oil, lanolin, and vitamin E.

In selecting the proportions of the ingredients employed, the glycerin, lanolin, and any oils should not be added to the point of leaving hair too oily, or oily looking. With respect to vitamin E, two 200 microgram capsules of vitamin E can be added per three ounce container. The fragrance should be in a sufficient amount to be only noticeable when the hair is close to a person's face. The composition of the invention should have a slightly stronger aroma than that of shampoo. The composition should not be so strong as to be received by persons in a room standing at a considerable distance from the person wearing the composition.

The composition of the invention can be packaged in a recyclable plastic container. It would have an upside-down look where it would rest, or stand on its lid. The gel composition would always be on the top, ready to be squeezed out.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved gel hairdressing composition that is low in cost, relatively simple in preparation, and which may advantageously be used to preclude hair from becoming stiff. With the invention, a gel hairdressing composition is provided which precludes a flaky build up from accumulating. With the invention, a gel hairdressing composition is provided which precludes a dulling of the hair's natural sheen. With the invention, a gel hairdressing composition is provided which provides cuff control. With the invention, a gel hairdressing composition is provided which provides good control to freshly shampooed hair.

With respect to the above description, it should be realized that the optimum compositional relationships between the ingredients of the invention include variations in amounts which are deemed readily apparent and obvious to those skilled in the art, and therefore, all relationships equivalent to those described in the specification are intended to be encompassed only by the scope of appended claims.

While the present invention has been fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

The invention claimed is:

1. A hairdressing gel composition consisting of: 60.00% by weight of deionized water, 25.00% by weight of SD alcohol 40, 0.75% by weight of PVP/VA copolymer, 0.10% by weight of carrageenan, 5.00% by weight of glycerin, 0.10% by weight of panthenol, 0.10% by weight of dimethicone, 0.50% by weight of methyl gluceth-20, 0.05% by weight of myreth-3 laurate, 0.50% by weight of ceteth-20, 0.10% by weight of tetrasodium EDTA, 1.00% by weight of carbomer 940, 0.25% by weight of triethanolamine, 0.10% by weight of methylchloroisothiazolinone, 0.10% by weight of methylisothiazolinone, 0.25% by weight of styrene/acrylate copolymer, 1.00% by weight of petrolatum, 1.00% by weight of vegetable oil, 1.00% by weight of coconut oil, 1.00% by weight of olive oil, 1.00% by weight of mineral oil, 0.10% by weight of microcrystalline wax, 0.50% by weight of lanolin, and 0.05% by weight of vitamin E.

2. A hairdressing gel composition consisting of: 11.95% by weight of deionized water, 40.00% by weight of SD alcohol 40, 2.25% by weight of PVP/VA copolymer, 0.40% by weight of carrageenan, 15.00% by weight of glycerin, 0.40% by weight of panthenol, 0.40% by weight of dimethicone, 2.00% by weight of methyl gluceth-20, 2.00% by weight of myreth-3 laurate, 2.00% by weight of ceteth-20, 0.40% by weight of tetrasodium EDTA, 2.00% by weight of carbomer 940, 1.25% by weight of triethanolamine, 0.40% by weight of methylchloroisothiazolinone, 0.40% by weight of methylisothiazolinone, 1.25% by weight of styrene/acrylate copolymer, 3.00% by weight of petrolatum, 3.00% by weight of vegetable oil, 3.00% by weight of coconut oil, 3.00% by weight of olive oil, 3.00% by weight of mineral oil, 0.75% by weight of microcrystalline wax, 2.00% by weight of lanolin, and 0.15% by weight of vitamin E.

3. A hairdressing gel composition consisting of:
36.00% by weight of deionized water, 32.15% by weight of SD alcohol 40, 1.50% by weight of PVP/VA copolymer, 0.25% by weight of carrageenan, 10.00% by weight of glycerin, 0.25% by weight of panthenol, 0.25% by weight of dimethicone, 1.00% by weight of methyl gluceth-20, 1.00% by weight of myreth-3 laurate, 1.00% by weight of ceteth-20, 0.25% by weight of tetrasodium EDTA, 1.50% by weight of carbomer 940, 0.75% by weight of triethanolamine, 0.25% by weight of methylchloroisothiazolinone, 0.25% by weight of methylisothiazolinone, 0.75% by weight of styrene/acrylate copolymer, 2.00% by weight of petrolatum, 2.00% by weight of vegetable oil, 2.00% by weight of coconut oil, 2.00% by weight of olive oil, 2.00% by weight of mineral oil, 0.5% by weight of microcrystalline wax, 1.00% by weight of lanolin, and 0.10% by weight of vitamin E.

* * * * *